(12) United States Patent
Boretius et al.

(10) Patent No.: US 11,247,042 B2
(45) Date of Patent: Feb. 15, 2022

(54) IMPLANTABLE ELECTRICAL CONTACT ARRANGEMENT

(71) Applicant: Neuroloop GmbH, Freiburg (DE)

(72) Inventors: Tim Boretius, Freiburg (DE); Fabian Kimmig, Freiburg (DE); Christina Sebastian Hassler, Reute (DE); Dennis Plachta, Vörstetten (DE)

(73) Assignee: NEUROLOOP GMBH, Freiburg (DE)

( * ) Notice: Subject to any disclaimer, the term of this patent is extended or adjusted under 35 U.S.C. 154(b) by 209 days.

(21) Appl. No.: 16/461,656

(22) PCT Filed: Nov. 17, 2017

(86) PCT No.: PCT/EP2017/079599
§ 371 (c)(1),
(2) Date: May 16, 2019

(87) PCT Pub. No.: WO2018/091656
PCT Pub. Date: May 24, 2018

(65) Prior Publication Data
US 2019/0351214 A1    Nov. 21, 2019

(30) Foreign Application Priority Data
Nov. 18, 2016 (DE) .................. 10 2016 222 710.6

(51) Int. Cl.
*A61N 1/05* (2006.01)
*A61N 1/375* (2006.01)
*A61N 1/36* (2006.01)

(52) U.S. Cl.
CPC .............. *A61N 1/05* (2013.01); *A61N 1/36* (2013.01); *A61N 1/36142* (2013.01); *A61N 1/3752* (2013.01)

(58) Field of Classification Search
CPC ........ A61N 1/05; A61N 1/36142; A61N 1/36; A61N 1/3752
See application file for complete search history.

(56) References Cited

U.S. PATENT DOCUMENTS 5,755,743 A  5/1998 Volz et al.
5,755,759 A  5/1998 Cogan
(Continued)

FOREIGN PATENT DOCUMENTS

DE  10 2011 009 857 B4  9/2012
DE  10 2011 078 982 A1  1/2013
(Continued)

OTHER PUBLICATIONS

International Search Report for PCT/EP2017/079599, dated Mar. 13, 2018; English translation submitted herewith (5 pgs.).

*Primary Examiner* — Lindsey G Wehrheim
(74) *Attorney, Agent, or Firm* — Fitch, Even, Tabin & Flannery LLP

(57) ABSTRACT

An implantable electrical contact arrangement is described which has at least one electrode body arrangement composed otherwise entirely of biocompatible, electrically insulating material, with at least one freely accessible electrode surface enclosed directly or indirectly by the biocompatible electrically insulating material. The invention is characterized in that the electrode body arrangement has a stack-shaped layer composite which provides at least one gold layer connected to an iridium layer via a diffusion barrier layer. The stack-shaped layer composite by being completely encapsulated by an SiC layer, with the exception of at least one surface region of the iridium layer facing to be directed away from the layer composite. The SiC layer has an SiC layer surface which is facing to be directed away from the stack-shaped layer composite and which is
(Continued)

A-A adjoined directly or indirectly by the biocompatible, electrically insulating material.

12 Claims, 2 Drawing Sheets

(56) References Cited

U.S. PATENT DOCUMENTS

| | | | |
|---|---|---|---|
| 6,102,753 | A | 8/2000 | Lindegren |
| 8,195,308 | B2 * | 6/2012 | Frank ................. A61N 1/37512 |
| | | | 607/122 |
| 9,192,757 | B2 * | 11/2015 | Seymour .................. A61N 1/04 |
| 10,022,537 | B2 | 7/2018 | Schuttler et al. |
| 2011/0003497 | A1 | 1/2011 | Pompan |
| 2012/0109296 | A1 | 5/2012 | Fan |
| 2012/0184836 | A1 | 7/2012 | Kolberg et al. |
| 2012/0193119 | A1 | 8/2012 | Kempf et al. |
| 2012/0232631 | A1 | 9/2012 | Frewin et al. |
| 2013/0096602 | A1 | 4/2013 | Kumar |
| 2017/0326362 | A1 | 11/2017 | Plachta et al. |

FOREIGN PATENT DOCUMENTS

| | | |
|---|---|---|
| DE | 10 2012 020 260 A1 | 7/2013 |
| DE | 20 2007 019 606 U1 | 4/2014 |
| DE | 10 2014 014 943 A1 | 4/2016 |
| EP | 0 910 435 B1 | 1/2003 |
| EP | 0 811 397 B1 | 3/2005 |
| EP | 2476455 A1 | 7/2012 |
| WO | 2011/066552 A2 | 6/2011 |

* cited by examiner

IMPLANTABLE ELECTRICAL CONTACT ARRANGEMENT

CROSS REFERENCE TO RELATED APPLICATIONS

Reference is made to PCT/EP2017/079599 filed Nov. 17, 2017, and German Application No. 10 2016 222 710.6 filed Nov. 18, 2016, which are incorporated herein by reference in their entirety.

BACKGROUND OF THE INVENTION

Field of the Invention

The invention relates to an implantable electrical contact arrangement, which has at least one electrode body arrangement composed otherwise entirely of a biocompatible, electrically insulating material, with at least one freely accessible electrode surface enclosed directly or indirectly by the biocompatible electrically insulating material.

Description of the Prior Art

Generic contact arrangements are used, for example, in electromechanical connectors, which in general have two mechanically detachable components that can be joined together for the purpose of at least one of electrical power and signal transmission, and are subject to specific requirements relevant to operational safety depending on their design and application. In the case of implantable connectors, they must meet the requirements for active implantable medical devices exposed to a permanently moist environment, and must be designed to withstand moisture or water penetration into the interior of the implant without damage for as long a period of time as possible.

Particularly critical in the case of implantable connectors which are known per se are the longitudinal joining sections on which the connector components are usually joined and interlocked in a form fit and a force fit. The particular challenge in the design and construction of such connectors is to prevent the penetration of water or moisture into and through the interfaces between the plug and socket parts incorporated inside a connector for as long as possible, in order to avoid water or moisture contact with the electrical structures incorporated inside a connector. Thus the contact of water on electrically conductive conductor and electrode structures, mostly made of metallic materials, leads to irreversible degradation phenomena and an associated impairment of the electrical power and signal transmission properties. In addition, the presence of water or moisture can cause detachments between the metallic structures incorporated inside the connector and the surfaces of the connector components that directly surround them, which are mostly made of polymeric materials, and can thereby reduce the service life of such connectors.

Implantable electrical connectors exist in large numbers and varieties. All embodiments of known art have at least in common that measures are taken which hinder, preferably completely prevent, the penetration of moisture, primarily in the form of body fluid, into the inner, electrically conductive layer structure. The following publications are examples of electromechanical connectors, which are known per se, and which disclose representative connectors in a non-exhaustive form: DE 10 2011 009 857 B4, EP 0 910 435 B1, DE 10 2012 020 260 B1, DE 20 2007 019 606 U1, and EP 0 811 397 B1.

An implantable connector known per se is illustrated in FIG. 2a, with a plug part 1 and a socket part 2. The plug part 1 can be fully inserted along its forward joining section 4 into the insertion opening 3 of the socket part 2. In the region of the joining section 4, only one electrode body 5 is attached, preferably raised above the surface of the plug part 1, for reasons of simpler presentation and explanation. In practice, connectors typically have a large number of such electrode bodies. When the plug part 1 is inserted, the electrode body 5 makes contact with a corresponding counter-electrode (not shown), attached on the inside of the socket part 2, for purposes of electrical signal or power transmission.

The plug part 1 also has a contact electrode surface 6 in a region of the plug part directed away from the joining section 4, onto which an external electrical supply cable 7 is attached, for example a soldered connection 8, and which provides an external electrical signal and power supply.

To illustrate the internal structure of the plug part 1, FIGS. 2b, c and d show cross-sections through the plug part 1 along the sections AA, BB and CC shown in FIG. 2a.

The plug part 1 has a housing 9, which is made of a biocompatible, preferably elastic, electrically non-conductive polymer, with the exception of the contact electrode surface 6 and the electrode body 5.

The electrode body 5 and the contact electrode surface 6 are made of platinum and are connected together integrally in the interior of the plug part 1. The platinum Pt electrode material is deposited on a silicon carbide substrate support 10, as can be seen in the cross-sectional illustrations shown in FIGS. 2b, c and d.

Although the connection between the SiC substrate support 10 and the platinum electrode material represents a preferred bonded connection, a degradation at the interface between the platinum and the SiC becomes apparent, especially with an increasing operating life and service life of such implanted connectors. Oxidation and hydration processes, caused by an electrical voltage applied continuously or in a pulsating manner to the electrode material, contribute to the formation of changes in the metallic lattice constant, which lead to deformations on the surface of the platinum electrode, as a result of which detachment phenomena occur at the interface between the platinum and the silicon carbide. Such processes inevitably lead to an irreversible loss of functionality of the implantable connector.

An implantable nerve electrode is described in the publication DE 10 2011 078 982 A1. It has a supporting substrate of medical silicone, into which conductor tracks are integrated, which connect electrode contacts and terminal contacts in each case. The conductor tracks, together with the electrode contacts and connection contacts, are made of stainless steel or platinum.

The publication DE 10 2014 014 943 A1 discloses an implantable electrode arrangement in which specially structured electrodes are embedded inside a supporting substrate of a biocompatible polymer. The electrodes each have electrode contact surfaces leading onto the supporting substrate surface, and otherwise have at least one electrode surface directed away from the supporting substrate surface, which has no access, or only very limited access, to the intracorporeal moist environment.

The US published patent application 2011/0034977 A1 describes an implantable electrode arrangement with a large number of electrodes mounted on a partly elastic deformable supporting body, all of which are connected to control units integrated inside the supporting body.

SUMMARY OF THE INVENTION

Underlying the invention is the designing of an implantable electrical contact arrangement, which has at least one electrode body arrangement composed otherwise entirely of a biocompatible, electrically insulating material, with at least one freely accessible electrode surface enclosed directly or indirectly by the biocompatible, electrically insulating material such that operational degradation phenomena, as explained above, do not occur or occur only to a negligibly small extent, so that the service life of contact arrangements is increased. In addition, the solution-compliant measures should contribute to improving the resistance of implantable electrical contact arrangements to moisture ingress caused by the prevailing intracorporeal moist environment.

In accordance with the invention, an implantable electrical contact arrangement in accordance with the invention is characterised in that the electrode body arrangement has a stack-shaped layer composite, which provides at least one gold layer connected to an iridium layer via a diffusion barrier layer. The stack-shaped layer composite is otherwise completely encapsulated by an SiC layer, with the exception of at least one surface region of the iridium layer directed away from the layer composite. The SiC layer, in turn, has an SiC layer surface, which is directed away from the stack-shaped layer composite, and which is adjoined directly or indirectly by the biocompatible, electrically insulating material.

By providing a diffusion barrier layer which is introduced between the gold layer and the iridium layer, of a transition metal, the lattice constant of which is smaller than the lattice constant of gold, but larger than the lattice constant of iridium, a stack-shaped layer composite is implemented, at the interfaces on which high cohesive bonding forces primarily act. That is, the bonding proportion of the cohesive bonding forces between the interfaces is at least 70%, preferably at least 80%, and in particular preferably at least 90%. The remaining bonding forces are based, for example, on covalent or adhesive bonds, or the like.

In a particularly preferred embodiment, platinum is used as a diffusion barrier layer, but the use of titanium is also possible. The solution-compliant stack-shaped layered composite, preferably having the layer sequence SiC, Au, Pt, Ir, has optimally matched lattice constants, which form an intimate stack-shaped layered composite based on strong cohesive bonding forces. This is reflected in the lattice constants of the following preferred layer sequence: SiC: 4.36 Å, Au: 4.07 Å, Pt: 3.92 Å, Ir: 3.83 Å.

The formation of carbides, which counteract the formation of cohesive bonding forces, can be excluded by the direct layer sequence of the SiC layer and the gold layer located on it. In addition, the layered composite of SiC and gold is temperature-stable up to temperatures of 550° C. maximum.

The platinum or titanium layer serves as a diffusion barrier and preferably only has a layer thickness of about 20 to 30 nanometers, both for the purpose of optimally matching the lattice constants inside the layer-shaped stacked composite, as mentioned above, and to prevent diffusion of gold into the adjacent Ir layer.

In a preferred embodiment of the electrical contact arrangement, the at least one surface region of the Ir layer, which is not covered by the SiC layer corresponds to the at least one electrode surface of the contact arrangement. In an advantageous further development it is also possible to apply additionally an iridium oxide layer onto the freely accessible iridium layer, which corresponds to the at least one electrode surface of the contact arrangement.

With the exception of the at least one freely accessible electrode surface in question, the entire electrode body arrangement is surrounded by the biocompatible, electrically insulating polymer, which is preferably a polyimide, a liquid crystal polymer (LCP), parylene, or polydimethylsiloxane (PDMS).

The stacked layered components, which is characterised by significantly high cohesive bonding forces between the layers, is particularly advantageously suitable for the construction of a plug and/or socket part of an implantable electrical plug connector, which is characterised in that the biocompatible, electrically insulating material comprising the at least one electrode arrangement bounds the surface of a body, which the at least one freely accessible electrode surface of the electrode body arrangement adjoins directly or indirectly.

In the case of a plug part, at least one further freely accessible electrode surface is provided on the surface of the body, by way of which an external signal or electrical power supply is preferably provided. The at least two electrode surfaces are electrically connected via an electrical connection running inside the body.

In a preferred embodiment, both freely accessible electrode surfaces are directly or indirectly connected to a gold electrical connection, which is integrally connected to the gold layer of the solution-compliant electrode body arrangement on one side and is otherwise completely enclosed by the SiC layer, which in turn is surrounded by the biocompatible, electrically insulating material of the body.

In the case of a socket part, in which at least one further freely accessible electrode surface need not necessarily be provided, the at least one freely accessible electrode surface inside the body is electrically connected to an electrical connection, which is connected to any intracorporeally positioned load.

Needless to say, the solution-compliant design of implantable electrical contact arrangement can also be integrated and used in other electrical components and systems that are exposed to a constant moist environment, and whose accessibility is at least limited, so that the longest possible system service life is required for an otherwise autonomous operation. For example, the contact arrangement is also suitable as a stimulation arrangement for the application of electrical impulses to intracorporeal tissue regions. Here the freely accessible contact electrode surface, preferably in the form of the above-mentioned iridium oxide layer, serves as an active stimulation electrode, which is brought into direct or indirect physical, and thus also electrically conductive, contact with a physiological tissue region, that is along a nerve or muscle, so as to stimulate it.

The iridium oxide layer also has a sufficiently porous electrode surface so that the electrochemically active electrode surface is many times larger than the geometrical electrode surface. This contributes, among other things, to a reduced impedance of the electrode surface, and drastically increases the maximum charge injection density.

BRIEF DESCRIPTION OF THE DRAWINGS

The invention will be described below in an exemplary manner by way of examples of embodiment with reference to the figures, without any limitation of the general inventive concept. Here:

FIGS. 2b, c and d show cross-sectional illustrations along the sections AA, BB, CC illustrated in FIGS. 2a.

DETAILED DESCRIPTION OF THE INVENTION

Figure 1A:
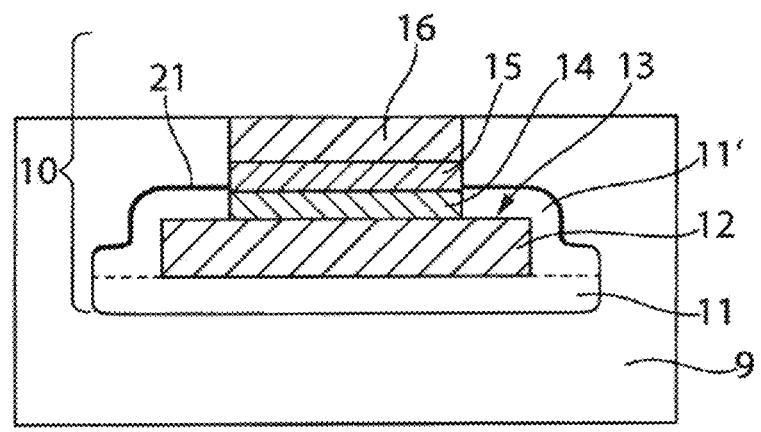
FIGS. 1a, b and c show cross-sectional illustrations of a plug part of an implantable connector arrangement.
Figure 2A:
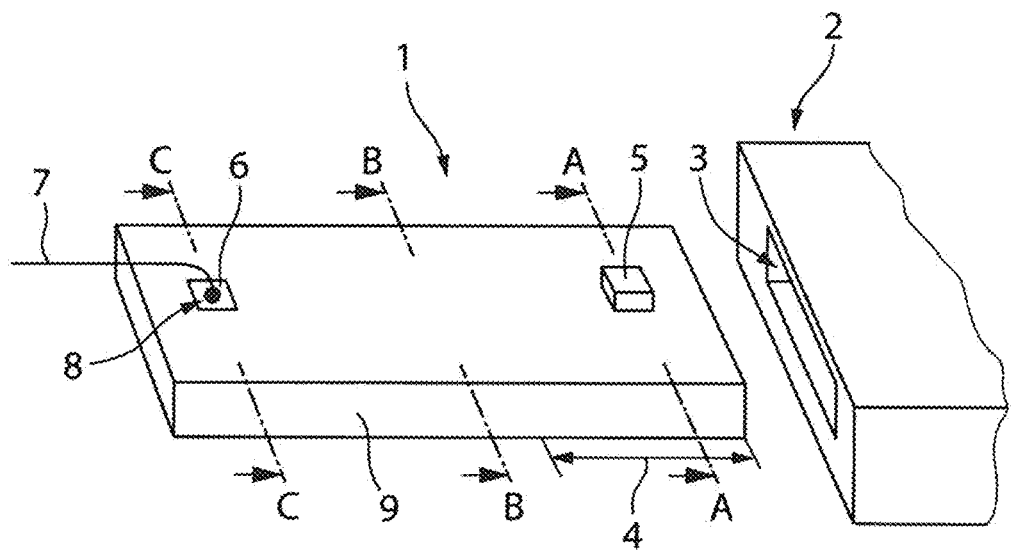
FIG. 2a shows a schematic plan view of an implantable connector in accordance with the prior art.
Figure 2B:
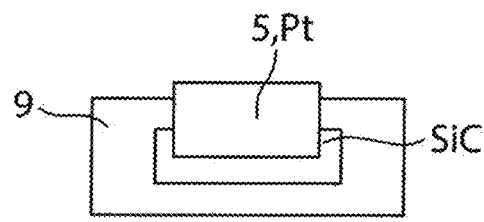
Figure 2C:
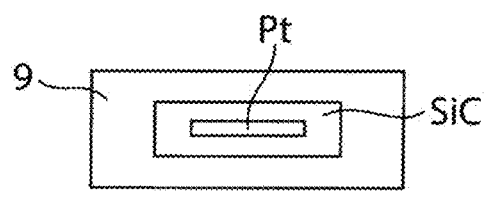
Figure 2D:
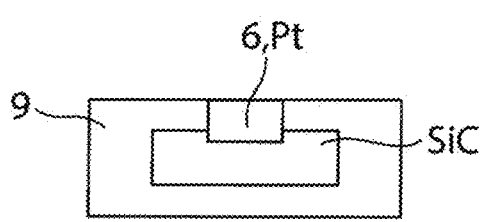

On the basis of the illustration in FIG. 2a of a plug part 1, which, just for reasons of clarity, has a single electrode body 5, together with a contact electrode surface 6 that is electrically connected to the electrode body 5. A large number of such electrode bodies 5 and corresponding contact electrode surfaces 6 are normally located on a plug part 1 that is known per se. In what follows a design of plug part is not visibly different externally from the known shape of a plug part. The design is reflected in the arrangement and structure of the electrode body arrangement integrated in the interior of the plug part 1, which in what follows is explained in more detail with reference to FIG. 1a.

FIG. 1a shows a cross-sectional view along a cross-sectional plane AA of a of the plug part 1, in accordance with the cross-section AA indicated in FIG. 2a. Inside a housing 9 made of a biocompatible, electrically insulating polymer, an electrode arrangement 10 is integrated, which is characterised by the following layer structure.

a gold layer 12 is deposited on an SiC layer serving as a supporting substrate 11, while a diffusion barrier layer 14 which is a platinum layer that is only a few 10 nm thick which is deposited on the surface 13 of the gold layer that is directed away from the supporting substrate 11. The diffusion barrier layer 14 covers only part of the gold layer surface 13. In plan view the diffusion barrier layer 14 remains laterally surrounded by a gold layer surface 13. The arrangement and formation of the three layers 14, 15 and 16, which are deposited on each other, is carried so that the three layers are flush with each other along the vertical stacking direction.

Both the gold layer 12, and the diffusion barrier layer 14, as well as the adjacent iridium layer 15 along at least a partial layer thickness are hermetically enclosed laterally by an additional SiC layer 11'. The SiC layer 11' is integrally bonded to the SiC layer serving as the supporting substrate 11. Another adhesion-promoting layer 21 of diamond-like carbon (DLC) is preferably deposited onto the upper SiC layer 11', which closes flush with the SiC layer 11'.

The electrode body arrangement 10 has the following layered composite which are SiC layers 11 and 11', a DLC layer 21, a gold layer 12, a diffusion barrier layer 14, an iridium layer 15, and an iridium oxide layer 16.

The entire electrode body arrangement 10 is embedded in a biocompatible, electrically insulating polymer, which is preferably a polyimide, a liquid crystal polymer, parylene, or PDMS; part of the iridium oxide layer 16 preferably protrudes from the polymer housing 9 and forms the contact surface of the electrode body 5, which, after appropriate insertion of the plug part 1 into the socket part 2, makes contact with a counter-electrode surface provided inside the socket part 2.

As already mentioned, titanium can also be used as a diffusion barrier layer 14 instead of platinum.

Figure 1B:
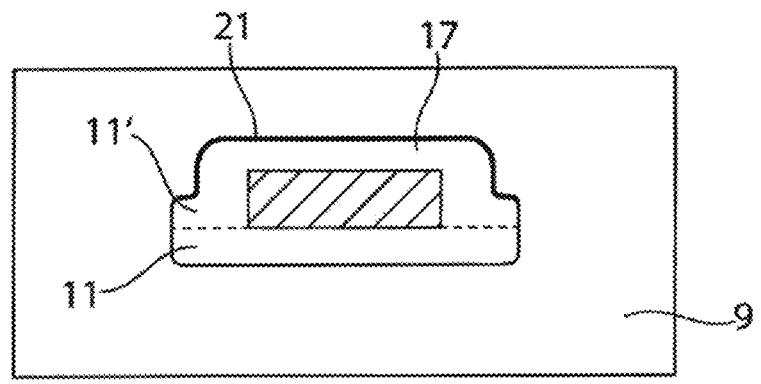

For the electrical connection of the iridium oxide layer 16, which corresponds to the electrode body 5 designated in FIG. 2a, with the contact electrode surface 6, a gold connecting line 17 running in the interior of the housing 9 is used, which is integrally connected on one side with the gold layer 12 of the electrode body arrangement 10. The gold connecting line 17 is completely encapsulated with an SiC layer 11/11' and is hermetically sealed from the polymer housing 9. See section BB in FIG. 1b.

Figure 1C:
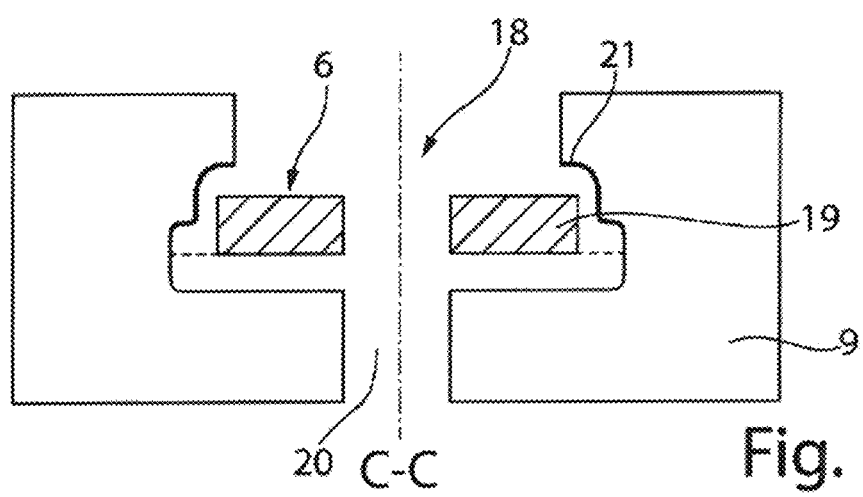

In the region of the contact electrode surface 6, see section CC in FIG. 1c. A recess 18 is introduced into the polymer housing 9, which provides free access to the surface of a gold contact layer 19, which is integrally connected to the gold connecting line 17. The gold contact layer 19 has a different shape, thickness and size from the gold connecting line 17, and is suitably adapted to form a contact electrode surface.

In particular, the freely accessible contact electrode surface 6 is completely laterally surrounded by the SiC layer 11', on which the DLC layer 21 is deposited. For the purpose of a permanent mechanical connection to an electrical supply line, the plug part at the location of the contact electrode surface 6 has a local, complete penetration in the form of a hole 20.

Both in the application of the implantable electrical contact arrangement as a plug part, as explained above, and in other implantable systems, such as in the form of a simulation electrode arrangement for electrical stimulation of intracorporeal body regions, the layered composite of SiC-DLC-Au—Pt—Ir-IrOx illustrated in FIG. 1a, very advantageously prevents water from penetrating between the individual layers.

REFERENCE LIST

1 Plug part
2 Socket part
3 Insertion opening
4 Joining section
5 Electrode body
6 Contact electrode surface
7 Electrical supply line
8 Soldered connection
9 Housing
10 Electrode body arrangement
11 SiC layer
11' SiC layer
12 Gold layer
13 Surface of the gold layer
14 Diffusion barrier layer
15 Iridium layer
16 Iridium oxide layer
17 Gold connecting line
18 Recess
19 Gold contact layer
20 Hole
21 DLC layer

The invention claimed is:

1. An implantable electrical contact arrangement, comprising:
   at least one electrode body composed entirely of a biocompatible electrically insulating material which encloses at least one electrode surface;
   a composite of stacked layers comprising at least one gold layer connected to an iridium layer via a diffusion barrier layer;
   the composite being encapsulated by an SiC layer, except for at least one surface region of the iridium layer; and
   the SiC layer including a surface which faces away from the composite and is joined to the biocompatible electrically insulating material; and wherein an iridium oxide layer is applied at least on the at least one surface region of the iridium layer that is not covered by the SiC layer which has an accessible surface facing away from the iridium layer which is the at least one electrode surface.

2. The contact arrangement in accordance with claim 1, wherein:
the biocompatible electrically insulating material is a polymer.

3. The contact arrangement in accordance with claim 2, wherein:
the polymer is one of a polyimide, a liquid crystal polymer, parylene, or PDMS.

4. The contact arrangement in accordance with claim 1, wherein:
the diffusion barrier layer comprises a transition metal having a lattice constant which is smaller than a lattice constant of gold and which is larger than a lattice constant of iridium.

5. The contact arrangement in accordance with claim 1, wherein:
the diffusion barrier layer is platinum or titanium.

6. An implantable contact arrangement, comprising:
at least one electrode body composed entirely of a biocompatible electrically insulating material which encloses at least one electrode surface;
a composite of stacked layers comprising at least one gold layer connected to an iridium layer via a diffusion barrier layer;
the composite being encapsulated by SiC layer except for at least one surface region of the iridium layer; and
the SiC layer including a surface which faces away from the composite and is connected to the biocompatible electrically insulating material; and wherein
the composite encapsulated by the SiC layer includes interfaces comprising one of SiC/Au, Au/Pt, and Pt/Ir; and
the composite has cohesive bonding forces.

7. The contact arrangement in accordance with claim 6, wherein:
a bonding proportion of cohesive bonding forces of at least 70% prevails between the interfaces.

8. An implantable electrical contact arrangement, comprising:
at least one electrode body composed entirely of a biocompatible electrically insulating material which encloses at least one electrode surface;
a composite of stacked layers comprising at least one gold layer connected to an iridium layer via a diffusion barrier layer;
the composite being completely encapsulated by SiC layer, except for at least one surface region of the iridium layer facing away from the composite; and wherein:
the SiC layer including a surface which faces away from the composite and is connected to the biocompatible electrically insulating material; and at least the diffusion barrier layer is hermetically surrounded by the gold, SiC and indium layers.

9. An implantable electrical contact arrangement, comprising:
at least one electrode body composed entirely of a biocompatible electrically insulating material which encloses at least one electrode surface;
a composite of stacked layers comprising at least one gold layer connected to an iridium layer via a diffusion barrier layer;
the composite being completely encapsulated by SiC layer except for at least one surface region of the iridium layer facing away from the composite; and
the SiC layer including a surface, which faces away from the composite and is connected by the biocompatible electrically insulating material; and wherein
the SiC layer is at least partially coated with an adhesion-promoting layer of diamond-like carbon (DLC).

10. A plug or socket part of an implantable electrical connector including at least one contact arrangement comprising:
at least one electrode body composed entirely of a biocompatible electrically insulating material which encloses at least one electrode surface;
a composite of stacked layers comprising at least one gold layer connected to an iridium layer via a diffusion barrier layer;
the composite being completely encapsulated by SiC layer except for at least one surface region of the iridium layer facing away from the composite;
the SiC layer including a surface which faces away from the composite and is connected to the biocompatible electrically insulating material;
the biocompatible electrically insulating material enclosing at least one electrode bordering a surface of a body with at least one electrode surface of the electrode body and at least one electrode surface; and
the electrode surfaces are electrically connected via an electrical connection inside the at least one electrode body.

11. The plug or socket part in accordance with claim 10, wherein
the electrical connection is connected to the gold layer of the electrode body;
the electrical connection is enclosed by a SiC layer which is surrounded by the biocompatible electrically insulating material of the electrode body; and
the accessible electrode surface is a surface of an electrode body which otherwise is enclosed by the SiC layer.

12. The plug or socket part in accordance with claim 10, wherein
the electrode body, the electrical connection, and the gold layer of the electrode body are connected and comprise gold.

* * * * *

UNITED STATES PATENT AND TRADEMARK OFFICE
CERTIFICATE OF CORRECTION

| | |
|---|---|
| PATENT NO. | : 11,247,042 B2 |
| APPLICATION NO. | : 16/461656 |
| DATED | : February 15, 2022 |
| INVENTOR(S) | : Tim Boretius et al. |

It is certified that error appears in the above-identified patent and that said Letters Patent is hereby corrected as shown below:

On the Title Page

Item (72) correct inventor #3, Christina Sebastian HASSLER, please delete "Sebastian".

Signed and Sealed this
Eighteenth Day of July, 2023

Katherine Kelly Vidal
*Director of the United States Patent and Trademark Office*